United States Patent [19]

Hollister et al.

[11] Patent Number: 5,352,459
[45] Date of Patent: Oct. 4, 1994

[54] USE OF PURIFIED SURFACE MODIFIERS TO PREVENT PARTICLE AGGREGATION DURING STERILIZATION

[75] Inventors: Kenneth R. Hollister, Chester Springs; David Ladd, Wayne; Gregory L. McIntire, West Chester; George C. Na, Fort Washington; Natarajan Rajagopalan, Phoenixville; Barbara O. Yuan, Villanova, all of Pa.

[73] Assignee: Sterling Winthrop Inc., New York, N.Y.

[21] Appl. No.: 991,639

[22] Filed: Dec. 16, 1992

[51] Int. Cl.$^5$ .................. A61K 9/14; A61K 47/34
[52] U.S. Cl. .................... 424/489; 514/951; 424/4
[58] Field of Search ............ 424/489, 497, 501, 4; 428/402, 402.24, 403, 407; 430/107, 111, 138; 502/8, 9, 402; 422/26; 514/951; 252/357

[56] References Cited

U.S. PATENT DOCUMENTS 5,145,684  9/1992  Liversidge et al. ............... 424/499

Primary Examiner—Edward J. Webman
Attorney, Agent, or Firm—William J. Davis

[57] ABSTRACT

This invention discloses a composition comprised of nanoparticles having a purified polymeric surfactant as a surface modifier adsorbed on the surface thereof and a cloud point modifier associated therewith, which cloud point modifier is present in an amount sufficient to increase the cloud point of the surface modifier. Preferred purified polymeric surfactants are purified polyalkyleneoxide substituted ethylenediamine surfactants. A preferred cloud point modifier is polyethylene glycol. This invention further discloses a method of making nanoparticles having a purified polymeric surfactant as a surface modifier adsorbed on the surface and a cloud point modifier associated therewith, comprised of contacting said nanoparticles with the cloud point modifier for a time and under conditions sufficient to increase the cloud point of the surface modifier.

9 Claims, 3 Drawing Sheets

USE OF PURIFIED SURFACE MODIFIERS TO PREVENT PARTICLE AGGREGATION DURING STERILIZATION

FIELD OF THE INVENTION

This invention relates to therapeutic and diagnostic compositions with a modified cloud point, and to a method for the preparation thereof.

BACKGROUND OF THE INVENTION

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm).

As a result of their small size, sterilization of therapeutic and diagnostic agents in nanoparticulate form stabilized by a surface modifier (surfactant) is difficult. Filtration using a filter of 0.22 $\mu$m mesh size is sufficient to remove most bacteria and viruses, but the nanoparticles, most of the time, due to their sizes, cannot be sterile filtered. Conventional autoclaving (steam heat) at 121° C. will result in substantial growth of particle size, rendering the resulting particles unusable.

The aggregation of nanoparticles upon heating is directly related to the precipitation and/or phase separation of the surface modifier (surfactant) at temperatures above the cloud point of the surfactant where the bound surfactant molecules are likely to dissociate from the nanoparticles and precipitate and/or phase separate, leaving the nanoparticles unprotected. The unprotected nanoparticles can then aggregate into clusters of particles. Upon cooling, the surfactant redissolves into the solution, which then coats the aggregated particles and prevents them from dissociating into smaller ones.

This invention is directed to novel compositions that allow autoclaving of nanoparticles with reduced or no particle size growth. These compositions provide for a modification of the surfactant adsorbed onto nanoparticles such that the nanoparticles do not agglomerate during autoclaving. This invention is also directed to a method of making such compositions.

BRIEF SUMMARY OF THE INVENTION

This invention is directed to a composition comprised of nanoparticles having a purified polymeric surfactant as a surface modifier adsorbed on the surface thereof and a cloud point modifier associated therewith, which cloud point modifier is present in an amount sufficient to increase the cloud point of the surface modifier.

This invention further discloses a method of making nanoparticles having a purified polymeric surfactant as a surface modifier adsorbed on the surface and a cloud point modifier associated therewith, said method comprising contacting said nanoparticles with the cloud point modifier for a time and under conditions sufficient to increase the cloud point of the surface modifier.

DETAILED DESCRIPTION OF THE INVENTION

Figure 1:
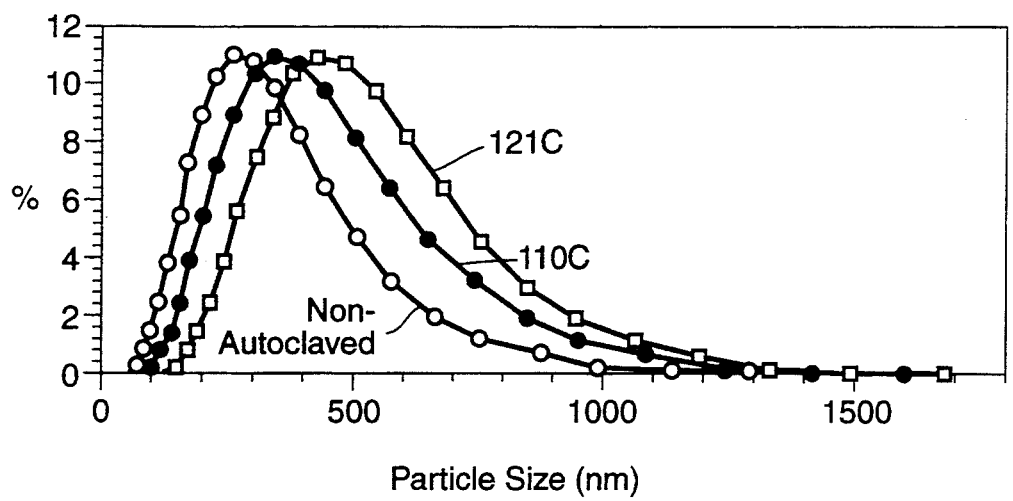
FIGS. 1-3 are particle size distributions of WIN 8883 (EEDA) particles containing T-908 surface modifier and PEG-400 cloud point modifier before and after autoclaving.
Figure 2:
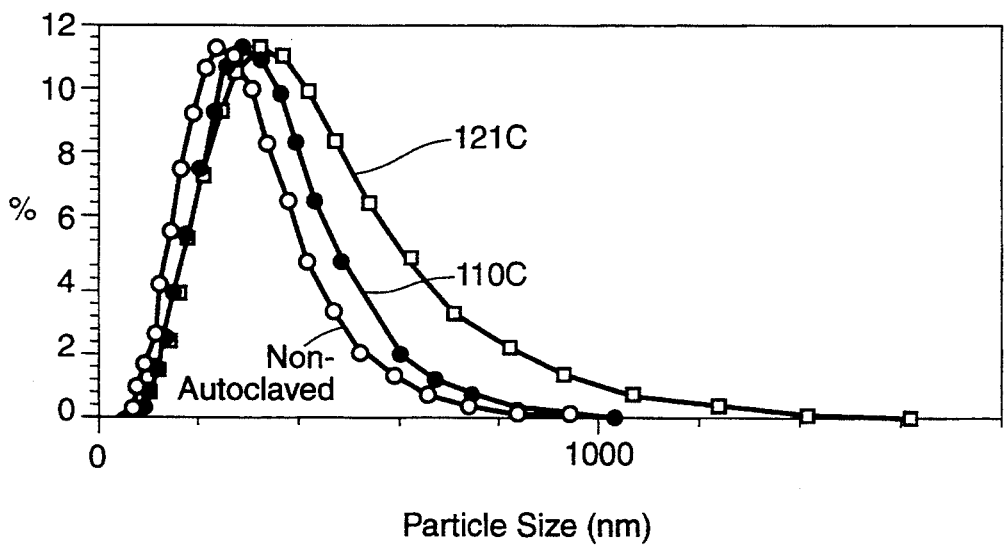
Figure 3:
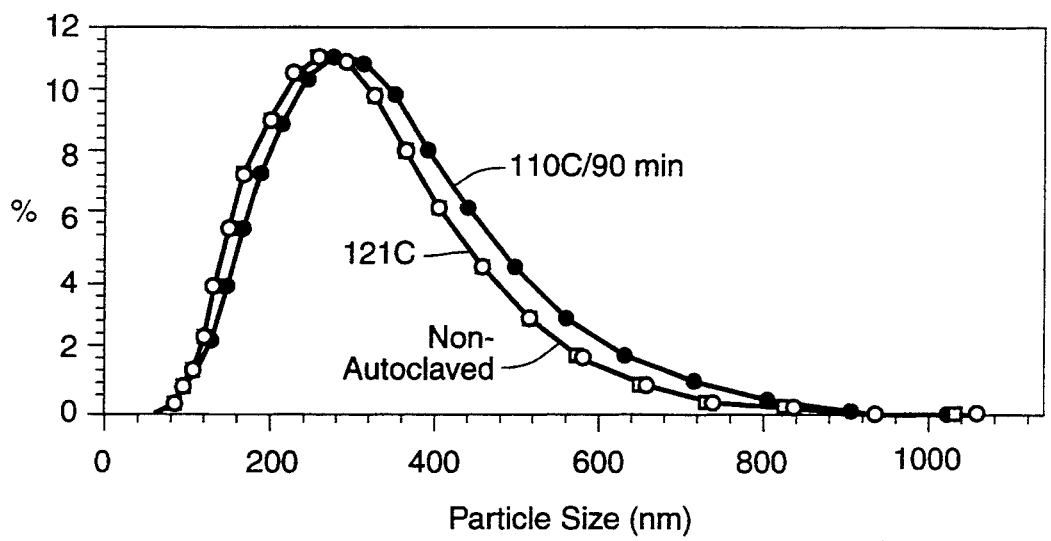
Figure 4:
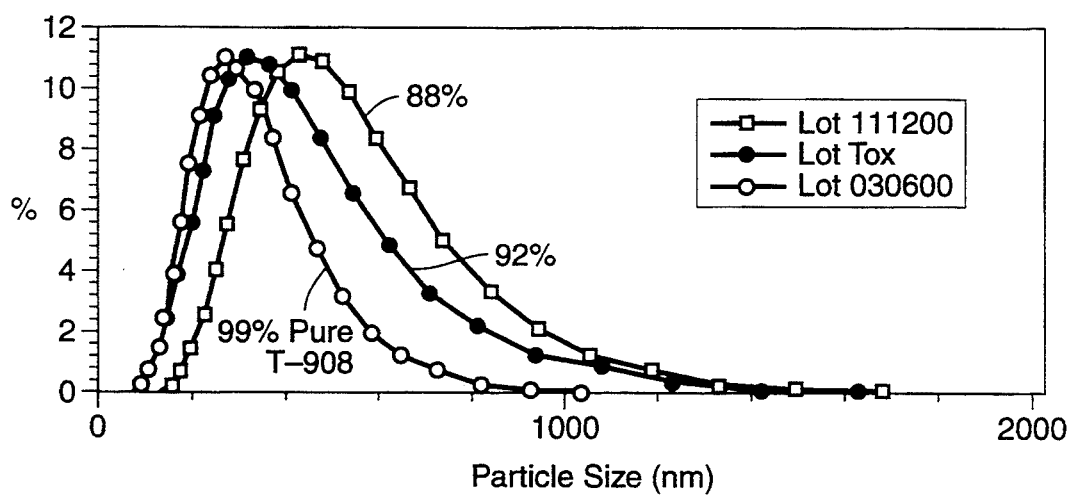
FIG. 4 is a particle size distribution of WIN 8883 (EEDA) particles containing T-908 surface modifier at 88%, 92% and 99% purity, and PEG-400 cloud point modifier after autoclaving at 121° C. for 20 minutes.
Figure 5:
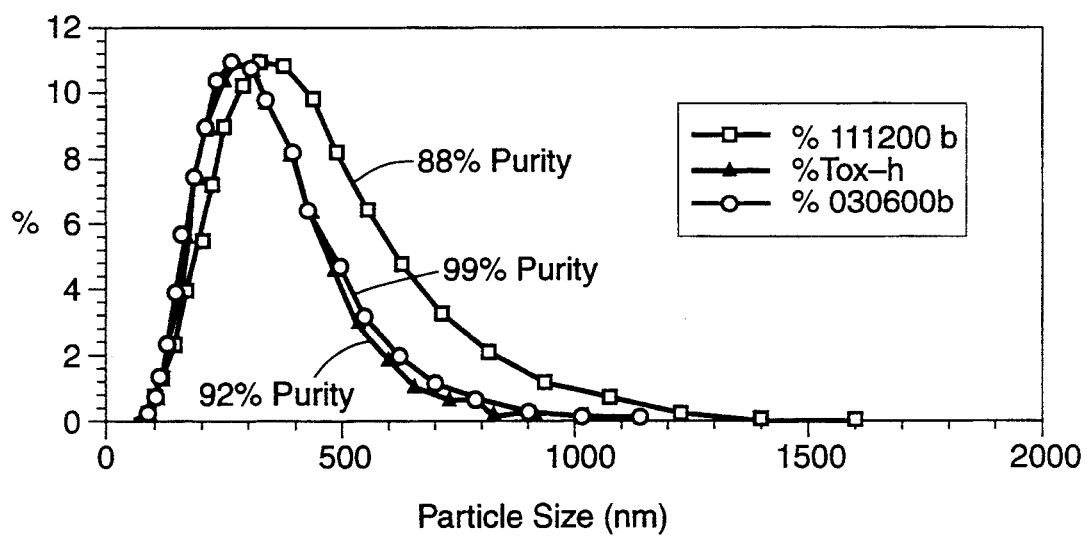
FIG. 5 is a particle size distribution of WIN 8883 (EEDA) particles containing T-908 surface modifier at 88%, 92% and 99% purity, and PEG-400 cloud point modifier after autoclaving at 110° C. for 90 minutes.
Figure 6:
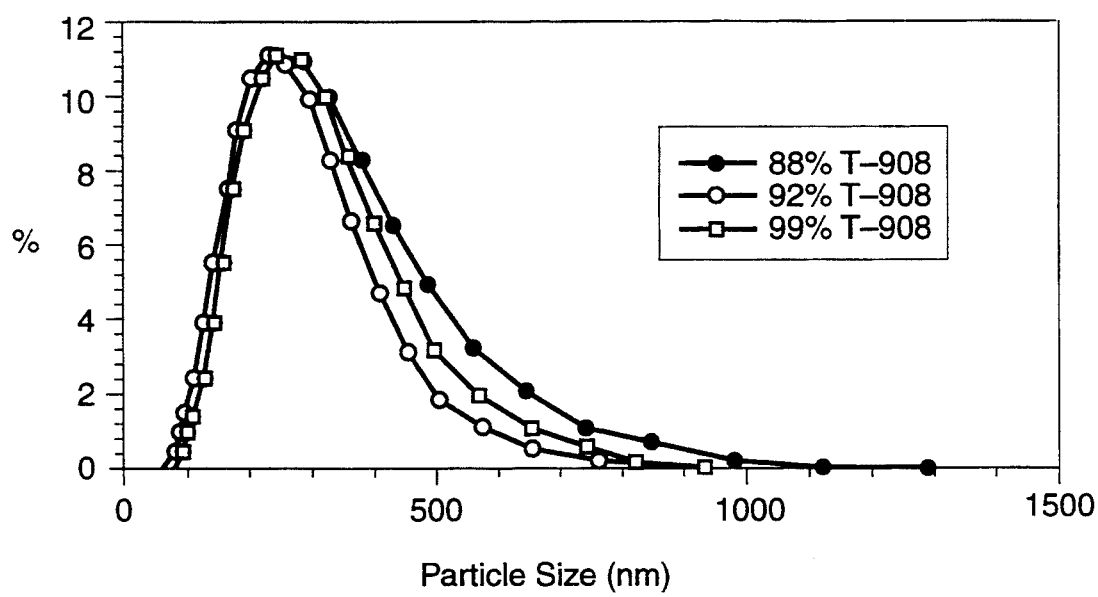
FIG. 6 is a particle size distribution of WIN 8883 (EEDA) particles containing T-908 surface modifier at 88%, 92% and 99% purity, and PEG-400 cloud point modifier before autoclaving.

This invention is directed to a composition comprised of nanoparticles having a purified polymeric surfactant as a surface modifier adsorbed on the surface thereof and a cloud point modifier associated therewith, which cloud point modifier is present in an amount sufficient to increase the cloud point of the surface modifier. In a preferred embodiment, the cloud point of the surface modifier is increased above the temperature for autoclaving of the nanoparticles to prevent agglomeration. The nanoparticles useful in the practice of this invention include a surface modifier. Surface modifiers useful herein physically adhere to the surface of the diagnostic or therapeutic agent in nanoparticle form, but do not chemically react with the agent or themselves. Individually adsorbed molecules of the surface modifier are essentially free of intermolecular crosslinkages. A surface modifier useful in the present invention is a purified polymeric surfactant.

A polymeric surfactant is a surfactant composed of 2 or more repeating monomeric units. Exemplary polymeric surfactants are Tetronic-908 (T-908) and Tetronic-1508 (T-1508), which are members of a family of polyalkyleneoxide substituted ethylenediamine surfactants having the following idealized structure:

$$\begin{array}{c} H-(O-CH_2-CH_2)_x-(O-\overset{\overset{\displaystyle CH_3}{|}}{CH}-CH_2)_y \\ H-(O-CH_2-CH_2)_x-(O-\underset{\underset{\displaystyle CH_3}{|}}{CH}-CH_2)_y \end{array} N-CH_2-CH_2-N \begin{array}{c} (CH_2-\overset{\overset{\displaystyle CH_3}{|}}{CH}-O)_y-(CH_2-CH_2-O)_x-H \\ (CH_2-\underset{\underset{\displaystyle CH_3}{|}}{CH}-O)_y-(CH_2-CH_2-O)_x-H \end{array}$$

They differ in that T-908 has a nominal average molecular weight of approximately 25,000 whereas T-1508 has a nominal average molecular weight of approximately 30,000. As supplied they contain a variety of impurities, including polymeric impurities whose structures have been identified as:

$$CH_2=CH-CH_2-O-(CH_2-\overset{\overset{\displaystyle CH_3}{|}}{CH}-O)_y-(CH_2-CH_2-O)_x-H$$

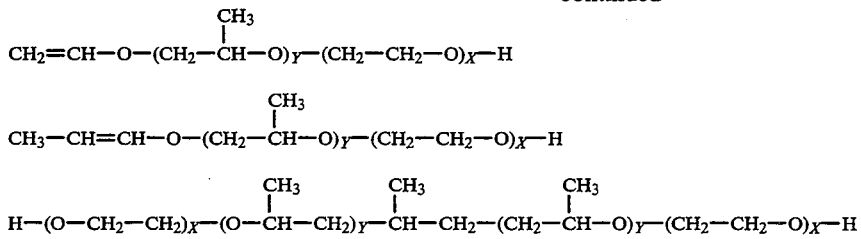

Analysis by size exclusion high pressure liquid chromatography (HPLC) indicates the total content of polymeric impurities in commercial samples of T-908 and T-1508 ranges from approximately 10 to over 30 percent. While non-polymeric impurities could be removed fairly readily, attempts to remove these polymeric impurities by conventional solvent washing and recrystalization techniques led only to modest reductions to a maximum of about half of the initial impurity content.

Another exemplary polymeric surfactant which has been purified is tyloxapol.

A purified polymeric surfactant is a polymeric surfactant that is substantially free of polymeric impurities according to the method of the present invention. This method involves the use of extensive aqueous diafiltration, as discussed in more detail elsewhere herein, extraction with nonaqueous solvents, or treatment with hydrophobic resins, ion exchange resins, and the like.

The phrase "substantially free of polymeric impurities" as used herein means that such impurities are present in the purified polymeric surfactant useful in the present invention in an amount of less than about 15 percent. Preferably, such impurities are present in an amount of less than about 10 percent, and more preferably in an amount of less than about 1 percent.

Alternatively, the amount of polymeric impurities in the initial sample of polymeric surfactant may be reduced by a factor of about 50 percent. Preferably, such reduction in the level of polymeric impurities is by a factor of about 90 percent, and more preferably by a factor of about 95 percent.

The polymeric surfactants are commercially available and/or can be prepared by techniques known in the art.

The nanoparticles useful in the practice of this invention can be prepared according to the methods disclosed in U.S. Pat. No. 5,145,684, whose disclosure is incorporated herein by reference. Briefly, nanoparticles are prepared by dispersing a poorly soluble therapeutic or diagnostic agent in a liquid dispersion medium and wet-grinding the agent in the presence of grinding media to reduce the particle size of the contrast agent to an effective average particle size of less than about 400 nm. The particles can be reduced in size in the presence of a surface modifier, e.g., during the wet grinding process.

A general procedure for preparing the particles useful in the practice of this invention follows. The therapeutic or diagnostic agent selected is obtained commercially and/or prepared by techniques known in the art as described above, in a conventional coarse form. It is preferred, but not essential, that the particle size of the coarse therapeutic or diagnostic substance selected be less than about 100 μm as determined by sieve analysis. If the coarse particle size of that agent is greater than about 100 μm, then it is preferred that the coarse particles of the therapeutic or diagnostic agent be reduced in size to less than 100 μm using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the surface modifier be present in the premix. The concentration of the surface modifier can vary from about 0.1 to 90%, and preferably is 1–75%, more preferably 10–60% and most preferably 10–30% by weight based on the total combined weight of the drug substance and surface modifier. The apparent viscosity of the premix suspension is preferably less than about 1000 centipoise.

The premix can be used directly by wet grinding to reduce the average particle size in the dispersion to less than 400 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, preferred media have a density greater than about 3 g/cm³. Zirconium oxide, such as 95% ZrO stabilized with magnesia, zirconium silicate, and glass grinding media provide particles having levels of contamination which are believed to be acceptable for the preparation of therapeutic or diagnostic compositions. However, other media, such as stainless steel, titania, alumina, and 95% ZrO stabilized with yttrium, are believed to be useful.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, and the like. The surface modifier preferably is present in an amount of about 0.1–10 mg per square meter surface area of the therapeutic or diagnostic agent. The surface modifier can be present in an amount of 0.1–90%, preferably 1–75%, more preferably 10–60%, and most preferably 10–30% by weight based on the total weight of the dry particle.

Therapeutic and diagnostic agents useful in the composition of the present invention include those disclosed in U.S. Pat. No. 5,145,684, whose disclosure is incorporated herein by reference. A preferred diagnostic agent is the ethyl ester of diatrizoic acid (EEDA).

As used herein, particle size refers to a mean particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a particle size of less than about 400 nm when measured by the above-noted techniques. In preferred embodiments of the invention, the effective average particle size is less than about 300 nm, and more preferably less than about 250 nm. In some embodiments of the invention, an effective average particle size of less than about 200 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

A method for the preparation of a nanoparticle composition according to this invention includes the steps of introducing a therapeutic or diagnostic agent, a liquid medium, grinding media, and optionally, a surface modifier into a grinding vessel; wet grinding to reduce the particle size of the therapeutic or diagnostic agent to less than about 400 nm; and separating the particles and optionally the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is carried out under aseptic conditions. Thereafter, the nanoparticle composition preferably is subjected to a sterilization process.

As noted elsewhere herein, sterile filtration very often will not provide adequate sterilization for nanoparticles. Therefore, other methods of sterilization are required. For example, steam or moist heat sterilization at temperatures of about 121° C. for a time period of about 15 minutes can be used. At altitudes near sea level, such conditions are attained by using steam at a pressure of 15 pounds per square inch (psi) in excess of atmospheric pressure.

Dry heat sterilization may also be performed, although the temperatures used for dry heat sterilization are typically 160° C. for time periods of 1 to 2 hours.

The cloud point is the temperature at which the surface modifier (surfactant) precipitates out of solution as described above. By the phrase "cloud point modifier" is meant a compound which influences the cloud point of surface modifiers. In particular, the cloud point modifiers useful in the present invention raise the cloud point of the surface modifiers found adsorbed onto nanoparticles. In this way, the surface modifiers do not dissociate from the surface of the nanoparticles at temperatures used in autoclaving. Therefore, nanoparticles thus modified do not agglomerate during the sterilization process, and thus retain their effective average particle sizes of less than about 400 nm after sterilization.

Examples of cloud point modifiers include nonionic compounds such as polyethylene glycols, e.g., PEG 400, available from J.T. Baker Chemical Co., propylene glycol, cyclodextrin, and ethanol; anionic surfactants such as sodium dodecylsulfate and dioctylsulfosuccinate; cationic surfactants such as cetrimide, fatty acids such as caprylic acid and capryonic acid; and charged phospholipids such as dimyristoyl phosphatidyl glycerol, cardiolipin and dimyristoylphosphatidylserine. A preferred cloud point modifier is polyethylene glycol.

The cloud point modifier is present in the compositions of the present invention in an amount sufficient to raise the cloud point of the purified polymeric surfactant. A preferred amount of cloud point modifier is 0.01% to 20% (w/v). A more preferred amount of cloud point modifier is 0.05% to 10% (w/v).

This invention further discloses a method of making nanoparticles having a purified polymeric surfactant adsorbed on the surface and a cloud point modifier associated therewith, comprised of contacting said nanoparticles with the cloud point modifier for a time and under conditions sufficient to increase the cloud point of the surface modifier.

This method involves the preparation of therapeutic or diagnostic nanoparticles, as discussed elsewhere herein, and contacting those nanoparticles with a cloud point modifier. Contacting may be by admixing a suspension of nanoparticles with a solution of cloud point modifier, followed by sterilization at a temperature and for a time sufficient to effect sterilization of the nanoparticle suspension.

The following examples further illustrate the invention and are not to be construed as limiting of the specification and claims in any way.

EXAMPLE 1: PURIFICATION OF T-908

A 2% solution of T-908 of 88% purity as determined by size exclusion HPLC (SEC-HPLC) with refractive index detection in $H_2O$ was prepared for the following diafiltration experiments:

(1) Approximately 50 mls of the 2% T-908 solution was placed in an Amicon 50 ml stirred cell with a YM-5 membrane and diafiltered against $H_2O$. Diafiltrate fractions were collected:

| Fraction | Amount |
|---|---|
| LDD-988-128-1-A | 43 ml |
| 1-B | 44 ml |
| 1-C | 17 ml |
| 1-D | 41 ml |
| | 145 ml |

Retentate was denoted as LDD-988-128-1 (approximately 50 ml), 88% pure by SEC-HPLC. (2) Approximately 50 mls of the 2% T-908 solution was placed in an Amicon 50 ml stirred cell with a YM-10 membrane and diafiltered against $H_2O$. Diafiltrate fractions were collected:

| Fraction | Amount |
|---|---|
| LDD-988-128-2-A | 32 ml |
| 2-B | 44 ml |
| 2-C | 35 ml |
| 2-D | 44 ml |
| | 155 ml |

Retentate was denoted as LDD-988-128-2 (approximately 50 ml), 93% pure by SEC-HPLC. Diafiltration of this retentate against $H_2O$ was continued: initially it was ultrafiltered down to approximately 20 ml, then diafiltered until a total of approximately 150 ml of ultrafiltrate plus diafiltrate was collected as LDD-988-128-2F; the retentate was denoted as LDD-988-128-2R (approximately 20 ml), 97% pure by SEC-HPLC.

The remainder of the T-908 2% solution (330 ml) was placed in an Amicon 400 ml stirred cell with a YM-10 membrane. This was then ultrafiltered down to approximately 130 ml, then diafiltered against $H_2O$ until approximately 1500 ml of ultrafiltrate plus diafiltrate was collected as LDD-988-129F; the retentate was denoted as LDD-988-129R, 96% pure by SEC-HPLC.

Diafiltration of this retentate against $H_2O$ was continued until approximately 1250 ml of diafiltrate was collected; the retentate was denoted as LDD-988-129R1 (approximately 105 ml), 98% pure by SEC-HPLC.

LDD-988-129F was concentrated in a stirred cell with a YM-3 membrane, then vacuum dried to yield 0.488 g of a white solid, denoted LDD-988-129X.

LDD-988-129X was determined to contain 74% low molecular weight (MW) impurity(s) and 26% high MW components by SEC-HPLC. Analysis of the NMR spectrum of this material has determined that it contains three olefinic compounds:

(1) a vinyl ether: $CH_2{=}CH\text{-}O\text{-}Polymer$;

(2) a propenyl ether: $CH_3CH{=}CH\text{-}O\text{-}Polymer$; and (3) an allyl ether: $CH_2{=}CHCH_2\text{-}O\text{-}polymer$.

EXAMPLE 2

A 5% solution of T-908 (lot WPMM-562B, 87% pure by SEC-HPLC) was prepared by dissolving 50.0 g of T-908 in 950 ml $H_2O$ 320 ml of the 5% T-908 solution was placed in an Amicon 400 ml stirred cell with a YM-10 membrane and diafiltered against $H_2O$. The diafiltration was stopped after 5760 ml (18 volumes) of diafiltrate was collected. The retentate (305 ml) was filtered (0.2 μm, nylon) giving LDD-988-150, 97% pure by SEC-HPLC. 100 ml of this solution was lyophilized to yield 4.55 g of a white solid denoted LDD-988-150A.

The remainder of the 5% T-908 solution (350 ml) was placed in Amicon 400 ml stirred cell with a YM-10 membrane and diafiltered against $H_2O$ until 8175 ml of diafiltrate was collected. The diafiltrate was ultrafiltered down to approximately 250 ml, filtered and lyophilized to yield 15.27 g of white solid denoted LDD-988-151, 95% pure by SEC-HPLC.

EXAMPLE 3

A sample of commercial T-908 Surfactant (BASF lot WPMM-562B) was extensively diafiltered under pressure using an Osmonics 52X-OPS-S2 spiral wound diafiltration membrane. The polymeric impurity level, determined by size exclusion HPLC, was reduced from an initial value of 12.7 percent to 2.4 percent after 10 turnovers of diafiltration, and subsequently to undetectable levels after 40 turnovers of diafiltration.

EXAMPLE 4

The purified surfactants were employed in the preparation of nanoparticulate dispersions of x-ray contrast agent and the cloud point modifier polyethylene glycol according to the methods of the present invention and provided stability against aggregration under the desired autoclaving conditions (121° C. for 20 rain) which was not achieved without this purification. These data are shown in Table 1 and FIGS. 1–6.

TABLE 1

| Sample Lot No. | Purity of T-908 | Mean Particle Size (nm) Initial | A* | B** |
|---|---|---|---|---|
| 111200 | 88% | 265 | 435 | 349 |
| GLP Tox | 92% | 242 | 326 | 291 |
| 030600 | 99% | 264 | 267 | 288 |

*Autoclaved for 121° C. for 20 minutes.
**Autoclaved for 110° C. for 90 minutes.

EXAMPLE 5: PURIFICATION OF T-1508

T-1508 (67.9% pure, as received measured by refractive index SEC-HPLC) was diafiltered using a polysulfone membrane (Osmonics 192T-HNO2, 15000 to 25000 MW cutoff, available from Osmonics, Inc.) until a purity of 92% was attained. Compared to the crude T-

1508, the purified T-1508 provided improved resistance to particle aggregation during heat sterilization.

The foregoing specification, including the specific embodiments and examples is intended to be illustrative of the present invention and is not to be taken as limiting. Numerous other variations and modifications can be effected without departing from the true spirit and scope of the present invention.

I claim:

1. A composition comprised of 0.1–60% by weight of nanoparticles consisting of therapeutic or diagnostic agent having 0.1–90% by weight of a purified noncrosslinked polymeric surfactant containing less than 15% impurities as a surface modifier adsorbed on the surface thereof and 0.01–20% by weight of a cloud point modifier associated with said polymeric surfactant and said therapeutic or diagnostic agent.

2. The composition of claim 1 wherein said nanoparticles contain a diagnostic agent.

3. The composition of claim 2 wherein said diagnostic agent is the ethyl ester of diatrizoic acid.

4. The composition of claim 1 wherein said purified polymeric surfactant is a purified polyalkyleneoxide substituted ethylenediamine surfactant.

5. The composition of claim 1 wherein said cloud point modifier is polyethylene glycol.

6. The composition of claim 1 wherein said cloud point modifier increases the cloud point of said surface modifier above 121° C.

7. A method for making the composition of claim 1 comprised of contacting said nanoparticles having said polymeric surfactant adsorbed on the surface thereof with said cloud point modifier.

8. The method of claim 7 further comprising the step of sterilizing said nanoparticle.

9. The method of claim 8 wherein said sterilizing is by steam heat autoclaving.

* * * * *